(12) United States Patent
Saunier (10) Patent No.: US 9,617,727 B2
(45) Date of Patent: Apr. 11, 2017

(54) FOLDABLE SENSORY ISOLATION BOOTH

(71) Applicant: Reperes, Paris (FR)

(72) Inventor: Franck Saunier, Paris (FR)

(73) Assignee: Reperes, Paris (FR)

( * ) Notice: Subject to any disclaimer, the term of this patent is extended or adjusted under 35 U.S.C. 154(b) by 0 days.

(21) Appl. No.: 14/902,802

(22) PCT Filed: Jul. 4, 2014

(86) PCT No.: PCT/EP2014/064328
§ 371 (c)(1),
(2) Date: Jan. 4, 2016

(87) PCT Pub. No.: WO2015/001086
PCT Pub. Date: Jan. 8, 2015

(65) Prior Publication Data
US 2016/0168847 A1     Jun. 16, 2016

(30) Foreign Application Priority Data

Jul. 5, 2013    (FR) ..................................... 13 56671

(51) Int. Cl.
| | |
|---|---|
| *E04B 1/82* | (2006.01) |
| *A61M 21/00* | (2006.01) |
| *E04H 1/12* | (2006.01) |
| *A61B 5/12* | (2006.01) |
| *E04B 1/343* | (2006.01) |
| *E04B 1/66* | (2006.01) |
| *E04B 1/84* | (2006.01) |
| *E04F 17/04* | (2006.01) |

(Continued)

(52) U.S. Cl.
CPC ............ *E04B 1/8218* (2013.01); *A61B 5/123* (2013.01); *A61M 21/0094* (2013.01); *E04B 1/34336* (2013.01); *E04B 1/34357* (2013.01); *E04B 1/66* (2013.01); *E04B 1/84* (2013.01); *E04F 17/04* (2013.01); *E04H 1/12* (2013.01); *E04H 1/125* (2013.01); *F24F 7/10* (2013.01); *E04B 1/3445* (2013.01); *E04H 3/08* (2013.01)

(58) Field of Classification Search
CPC .... F24F 7/10; E04F 17/04; E04H 1/12; E04B 1/34336; E04B 1/34357; E04B 1/8218; E04B 1/66; E04B 1/84; E04B 1/34345; A61B 5/123
USPC ...... 52/79.5, 64, 66, 67, 68, 69, 70, 71, 143
See application file for complete search history.

(56) References Cited

U.S. PATENT DOCUMENTS 2,837,777 A * 6/1958 White ....................... E04H 1/12
                                                        135/87
3,018,857 A * 1/1962 Parham ................. E04H 15/001
                                                       135/901

(Continued)

*Primary Examiner* — Brian Glessner
*Assistant Examiner* — Adam Barlow
(74) *Attorney, Agent, or Firm* — Adams and Reese LLP (57) ABSTRACT

The invention relates to a sensory deprivation booth foldable between a folded transport position and an unfolded usage position forming a closed space for receiving a user to perform a sensory analysis; the booth comprising: walls, each wall being airtight or suitable for filtering the flow of air passing through the wall; airtight articulations and closing devices, positioned at the joint of the walls and connecting the walls in an airtight manner in the unfolded usage position of the booth, the folded joints allowing superposition of the walls on one another in the transport position of the booth.

14 Claims, 4 Drawing Sheets

(51) Int. Cl.
  *F24F 7/10*   (2006.01)
  *E04B 1/344*  (2006.01)
  *E04H 3/08*   (2006.01)

(56) References Cited

U.S. PATENT DOCUMENTS

| | | | | |
|---|---|---|---|---|
| 3,629,875 | A * | 12/1971 | Dow | A47K 3/325 |
| | | | | 135/902 |
| 3,766,844 | A * | 10/1973 | Donnelly | F24F 3/1603 |
| | | | | 135/116 |
| 4,000,749 | A * | 1/1977 | Busco | A61G 10/005 |
| | | | | 135/117 |
| 4,928,581 | A * | 5/1990 | Jacobson | B08B 15/026 |
| | | | | 135/117 |
| 4,934,396 | A * | 6/1990 | Vitta | E04H 15/46 |
| | | | | 135/139 |
| 5,271,423 | A * | 12/1993 | Eychaner | E04H 15/001 |
| | | | | 135/134 |
| 5,533,305 | A * | 7/1996 | Bielecki | A61L 2/022 |
| | | | | 297/343 |
| 5,558,112 | A * | 9/1996 | Strieter | B09B 3/0066 |
| | | | | 134/103.2 |
| 6,833,122 | B2 * | 12/2004 | Reisfeld | A61L 9/205 |
| | | | | 422/186.3 |
| 7,134,444 | B2 * | 11/2006 | Mintie | B08B 15/00 |
| | | | | 135/131 |
| 7,552,563 | B2 * | 6/2009 | Becker | B42D 15/042 |
| | | | | 229/108 |
| 7,997,004 | B1 * | 8/2011 | Adrian | E04H 15/12 |
| | | | | 126/109 |
| 2004/0074212 | A1 * | 4/2004 | Yachi | A61G 10/005 |
| | | | | 55/385.2 |

* cited by examiner

Fig. 1

Fig. 6

FOLDABLE SENSORY ISOLATION BOOTH

This application is the U.S. national stage under 35 U.S.C. §371 of International Application No. PCT/EP2014/064328 (published as WO2015/001086A1), filed Jul. 4, 2014, which claims priority to French Application No. 13 56 671, filed Jul. 5, 2013.

The present invention relates to a foldable sensory isolation booth.

In the field of sensory analysis it is known to place the participants in a study in sensory analysis premises located within laboratories, the internal environment of which is controlled. In particular, the humidity and the temperature are generally controlled and the air is generally filtered in such laboratories.

The main problem with these laboratories is that they are expensive and complex to set up so that the number and the accessibility of the laboratories is limited.

In addition, the environment may differ from one laboratory to another so that the results of the sensory analyses are difficult to reproduce and can therefore be false.

There is therefore a need for sensory analyses in a more stable environment which is more accessible to the general public.

To this end, the present invention proposes a sensory isolation booth that is foldable between:
 a folded transport position and
 an unfolded position of use forming a closed volume for receiving a user to perform a sensory analysis;
 the booth comprising:
 walls, each wall being airtight or suitable for filtering the circulation of air through the wall;
 airtight articulations and closing devices positioned at the join of the walls,
 the articulations and closing devices, when closed, connecting the walls in an airtight manner in the unfolded position of use of the booth,
 the folded articulations allowing the superposition of the walls on one another in the transport position of the booth.

According to the preferred embodiments, the invention comprises one or more of the following features:
 the dimensions and the number of walls are chosen so that the closed reception volume in the position of use is greater than or equal to 1.9×1×1=1.5 m³, preferably greater than or equal to 1.9 m³ and the volume of an external parallelepiped cover for the booth in the transport position is less than or equal to 0.5 m³, preferably less than or equal to 1×1.9×0.1=0.2 m³.
 the external parallelepiped cover for the booth in the transport position has a length less than or equal to 2.5 m, preferably less than or equal to 2 m, a width less than or equal to 1.5 m, preferably less than or equal to 1.1 m and a depth less than or equal to 0.3 m, preferably less than or equal to 0.1 m.
 the weight of the booth being less than or equal to 25 kg, preferably less than or equal to 23 kg.
 the walls are made of a cellular material, preferably cellular PVC.
 the walls comprise a first and a second wall made of the same common material, the first and the second walls being connected to each other in an airtight manner by the common material which is thinned locally in order to form one of the articulations.
 the walls comprise a wall forming a door or an access hatch to the closed reception volume, the door or the hatch comprising an airtight closing device which closes magnetically.
 the walls comprise:
 at least one horizontal wall comprising an upper wall and preferably a lower wall;
 side walls;
 the airtight closing devices of the booth comprising, at the join of the at least one horizontal wall and the side walls in the unfolded position of use of the booth, an airtight closing device comprising at least one elastomer seal and a groove, the airtightness at the join of the at least one horizontal wall and the side walls being produced by compression of the airtight closing device between the side walls and the at least one horizontal wall under the effect of the weight of the walls.
 the walls comprise a wall equipped with a filter cartridge suitable for filtering the air circulating through the wall.

The invention also proposes a system for sensory analysis comprising:
 a controlled mechanical ventilation system;
 the above booth comprising an opening suitable for being connected in an airtight manner to the controlled mechanical ventilation system in order to change the air in the closed reception volume in the position of use.

Other features and advantages of the invention will become apparent on reading the description which follows of a preferred embodiment of the invention provided by way of example and with reference to the attached drawings.

A sensory isolation booth is proposed. The sensory isolation envisaged by the booth makes it possible to perform sensory analyses corresponding, for example, to visual, olfactory, organoleptic or even tactile analyses of a product.

Figure 1:
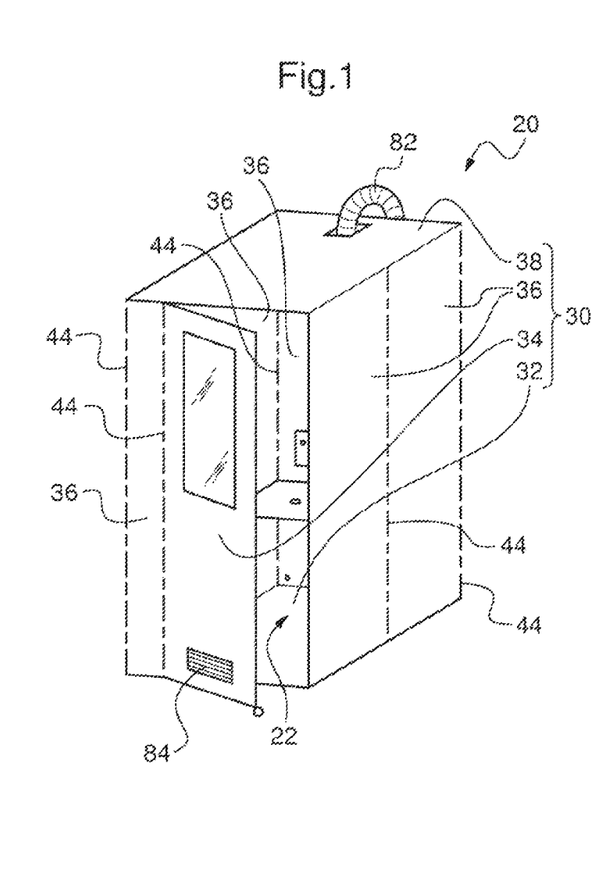
FIG. 1 shows a perspective view of a sensory isolation booth in a position of use and according to an embodiment.

FIG. 1 shows the booth 20 according to an embodiment in a position of use. This booth 20 forms a volume 22 for receiving a user (not shown) to perform a sensory analysis. The proposed sensory isolation booth 20 therefore has, for example, dimensions suitable for receiving a person, for example of adult size, the reception volume 22 being able to be greater than or equal to 1.5 m$^3$, and preferably greater than or equal to 1.9 m$^3$.

As illustrated, in the position of use, the reception volume 22 of the booth can be closed, in this case by means of a door 34. The closed nature, i.e. isolated, of the reception volume 22 formed by the booth 20 in the position of use makes it possible to control the conditions of the sensory analysis inside the booth 20. In the case, notably, of visual analyses, the closed nature of the volume 22 makes it possible to control the lighting. It is also possible to envisage the control of a set of other parameters influencing the user's sensory perception: maintaining the temperature, the humidity, soundproofing with respect to the external environment. In the most likely case of olfactory or organoleptic analyses, the closed nature of the volume 22 makes it possible to control the quality of the air in the booth 20 by limiting the entry of interfering odours from the outside into the inside of the booth 20. In the position of use, the proposed booth 20 with its closed reception volume 22 thus makes it possible to reduce external disturbances, notably olfactory disturbances, to the user during a sensory analysis carried out in the booth 20.

With the same aim of limiting external disturbances such as the entry of interfering odours from the outside into the inside, the walls 30 forming the booth 20 are airtight. The door 34 is part of the set 30 of walls 32, 36 and 38 forming the sensory booth 20. The walls 32 and 38 represented here are horizontal walls in the position of use, wall 32 being the lower wall of the booth 20, for example a mat, and wall 38 being the upper wall of the booth 20, otherwise called the roof. The walls 36 correspond to the vertical walls forming the booth 20 including the door 34 which is a particular variant of one of the vertical walls 36 of the booth 20. In the rest of this document, the term "wall 30" refers to any wall of all of the walls forming the booth 20 without differentiating while the reference numbers 32, 34, 36 and 38 refer specifically to each type of wall described above.

Figure 2:
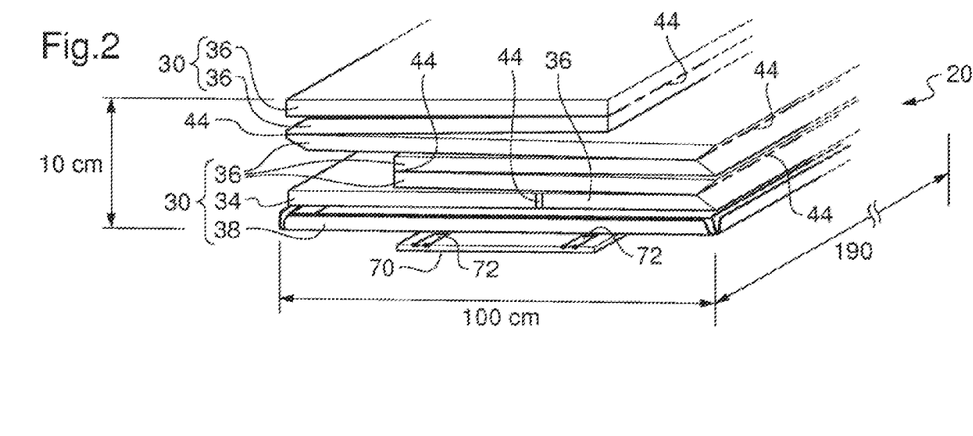
FIG. 2 shows a partial perspective view of the booth of FIG. 1 in the transport position.

In addition to a position of use, the proposed booth 20 has a transport position. FIG. 2 shows a partial perspective view of the booth 20 according to the embodiment of FIG. 1 in the transport position. As illustrated, the walls 34, 36 and 38 of the booth 20 are superposed on one another in the transport position. The transport position of the booth 20 is compact which facilitates transport of the booth. FIG. 2 represents in cm the dimensions of an external parallelepiped cover for the booth 20 in the transport position. According to the embodiment illustrated, the external parallelepiped cover has a length of 190 cm, a width of 100 or 106 cm and a depth of 10 cm. However, other dimensions can be envisaged for compactness in the transport position, such as:
- a length less than or equal to 2 m or even less than or equal to 2.5 m;
- a width less than or equal to 1.1 m or even less than or equal to 1.5 m;
- a depth less than or equal to 0.15 m or even less than or equal to 0.3 m.

In order to reduce the size of the booth 20 in the transport position still further, the lower wall 32 of the booth 20 (not shown in FIG. 2) can be omitted, the floor of a room being sufficient to close the reception volume 22 of the booth 20 in the position of use. Alternatively, the lower wall 32 can be formed by a flexible mat which is easy to roll up and which can be arranged in the external parallelepiped volume shown in FIG. 2. Depending on the dimensions and the number of walls 30 of the booth 20, the volume of the external parallelepiped cover can thus be less than or equal to 0.5 m$^3$ or even be less than or equal to 0.2 m$^3$ in accordance with the dimensions shown in FIG. 2.

In order to allow the proposed booth 20 to be changed from the position of use to the transport position and vice versa, it is a foldable booth. The position of use shown in FIG. 1 corresponds to the unfolded position while the transport position shown in FIG. 2 corresponds to the folded position. The proposed booth 20 comprises articulations at the joins between some of the walls 30 making it possible to fold and unfold the booth 20. In this document, a join between two walls 30 corresponds to the intersection formed between the two adjacent walls 30 in the position of use of the booth 20. A join between two walls 30 in the position of use of the booth 20 separates in the transport position into a lip on one of the walls 30 and a lip on the other of the walls 30. In this document, the two lips of the same join have the same reference number as the join itself.

Figure 3:
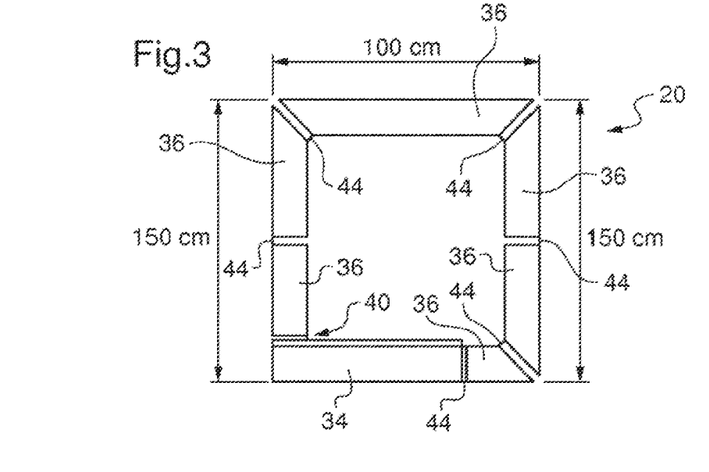
FIG. 3 shows a top view of the booth of FIG. 1.

FIG. 3 shows a top view of the booth 20 with the upper wall 38 omitted. As illustrated, the walls 36 and the door 34 are connected two by two by the articulations positioned at each join 44 between two adjacent walls 34 or 36. In this application, the articulations are represented by dot-and-dash lines. In the position of use of the booth 20, the articulations can be folded or unfolded along the walls 34 or 36 which connect them. The articulation at the join between the door 34 and the adjacent wall 36 can thus be unfolded when the door 34 is closed, while the articulation at the join between this same wall 36 and the adjacent wall 36 is folded in the position of use of the booth.

Figures 4, 5:
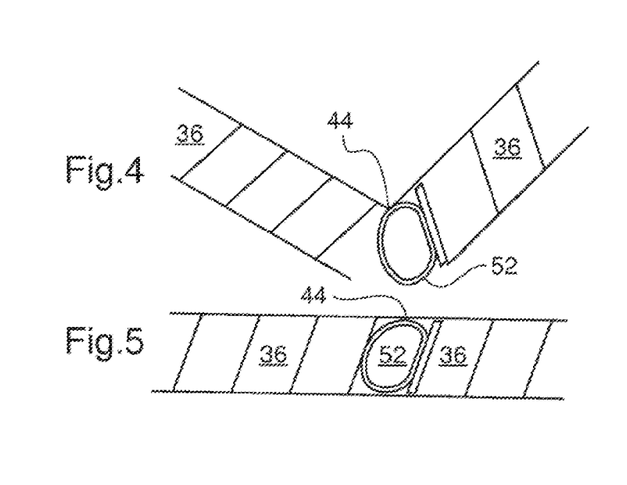
FIGS. 4 and 5 show an enlarged view of an embodiment of an articulation connecting two adjacent walls of the booth in a folded position and an unfolded position, respectively.

FIGS. 4 and 5 show an enlarged view of an embodiment of an articulation connecting two adjacent walls in a folded position and an unfolded position, respectively. According to the embodiment illustrated, the two walls 36 are made of the same common material, in this case a cellular material, and these two walls 36 are connected to each other by this common material which forms the articulation at the join 44. The articulation is then formed by a local thinning of the common material between the two walls 36. As shown in FIGS. 4 and 5, the local thinning of the common material corresponds to cutting the cellular material so that only one of the layers of the cellular material ensures the continuity of material between the two walls 36. Such a continuity of material between the two walls in an airtight material ensures that the articulation is airtight. The articulation may also comprise a hollow joint 52 ensuring sound and/or thermal insulation between the two lips of the join 44. Other embodiments of airtight articulation can be envisaged such as attached hinges, for example adhesive, and covered with an airtight material along the join between the walls 30. However, the embodiment shown in FIGS. 4 and 5 is preferred because of its simplicity and lightness.

In terms of the joins without airtight articulations, the booth 20 comprises airtight closing devices for closing the volume 22 in the position of use of the booth 20.

In other words, the joins between the adjacent walls 30 of the booth 20 are:
- either fixed as in the case of airtight articulations;
- or removable as in the case of airtight closing devices.

In all of the embodiments of joins proposed, the walls 30 can move with respect to each other at their join which makes it possible for the booth 20 to change from the position of use to the transport position where the walls 30 are superposed on one another, and vice versa.

The removable nature of the airtight closing device makes it possible to maintain the airtightness of the closed reception volume 22 while making it possible to separate the walls 30 locally and easily. This separation can make it possible, in the position of use, to access the interior of the booth 20 rapidly without dismantling the booth 20. This separation of the walls 30 also makes it possible, in the transport position, to contribute to the compactness of the booth 20. As shown in FIG. 2, the upper wall 38 can thus be completely separated from the walls 36 in order to facilitate transport.

Figure 6:
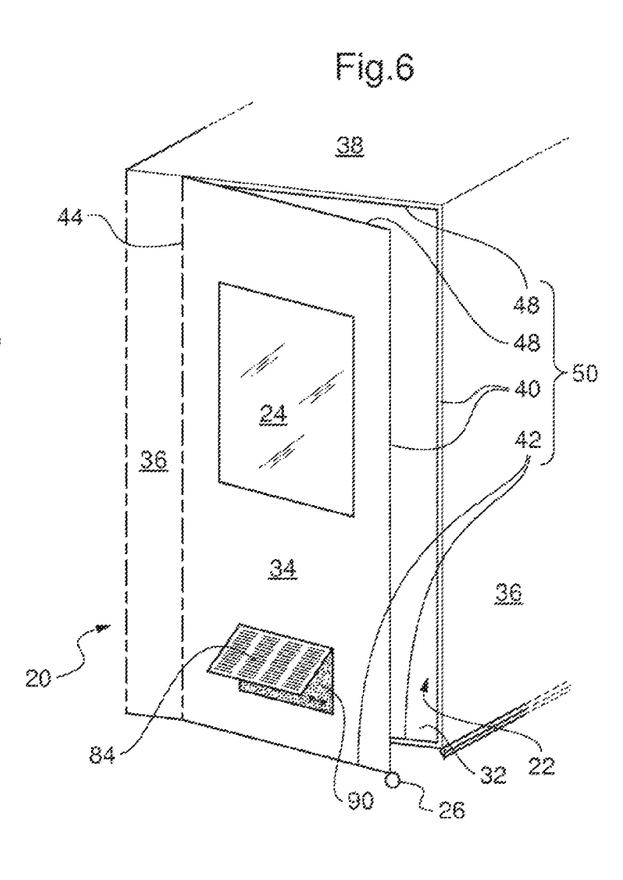
FIG. 6 shows the joins between the door of the booth and the walls adjacent to the door of the booth.

FIG. 6 shows the joins between the walls 38, 36 and 32 on the one hand and the door 34 on the other hand, joins in which the airtight closing devices are arranged. If the door 34 is open as shown, the two lips of a particular join 50 of the door can be separated. The join 48 connecting the door 34 and the upper wall 38, the join 40 connecting the door 34 and the side wall 36 and the join 42 connecting the door 34 and the lower wall 32, can thus each be separated into two lips on the walls 34 and 36 respectively which these joins connect. The airtight closing device of each join can be present on only one of the two lips of the join or on the two lips of the join according to the embodiments of the airtight closing device.

Figures 7, 15, 16, 17, 18, 19:
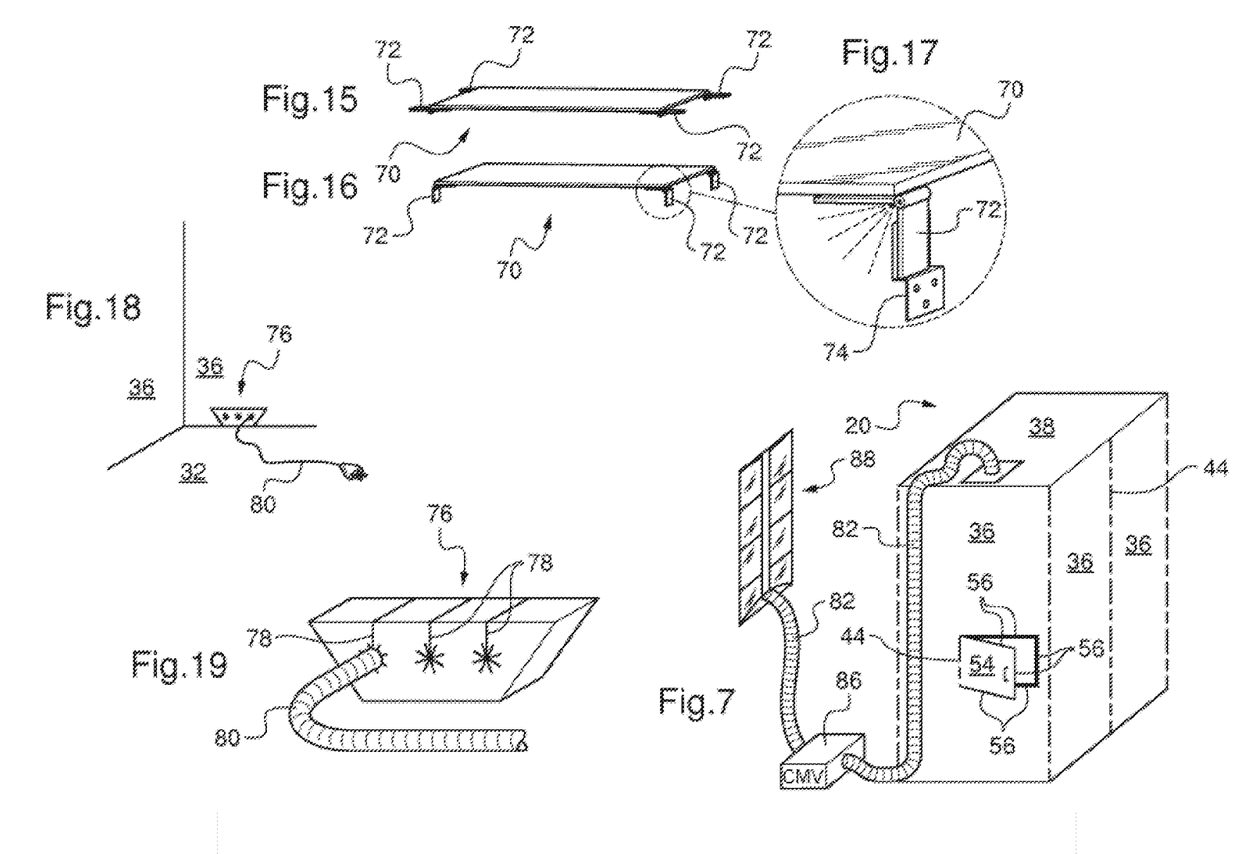
FIG. 7 shows a perspective view of the rear of the booth of FIG. 1.
FIGS. 15 and 16 show a shelf 70 with brackets placed flat and in a perpendicular position, respectively.
FIG. 17 shows an enlarged view of a bracket of the shelf of FIGS. 15 and 16 received in a support of a wall of the booth.
FIG. 18 shows a foam block in the shape of a trapezoidal wedge for connections to pass between the inside and outside of the booth.
FIG. 19 shows an enlarged view of the wedge of FIG. 18.

According to an embodiment, the closing device between two adjacent walls in the position of use can close magnetically. The magnetic airtight closing device can be formed by magnetic strips coated with silicone positioned on each of the two lips of a join. Magnetic airtight closing devices are preferably used for the wall forming the door 34 or for any other wall forming a removable access opening to the volume 22 of the booth 20 in the position of use. FIG. 7 shows a perspective view of the rear of the booth 20. As illustrated, the booth 20 preferably comprises an access hatch 54 to the volume of the booth, or a serving hatch. The airtightness of the hatch 54 with the other walls 30 of the booth is preferably produced by an airtight articulation at the join 44 and by the magnetic airtight closing devices at the joins 56.

Figures 8, 9, 10, 11, 12, 13, 14:
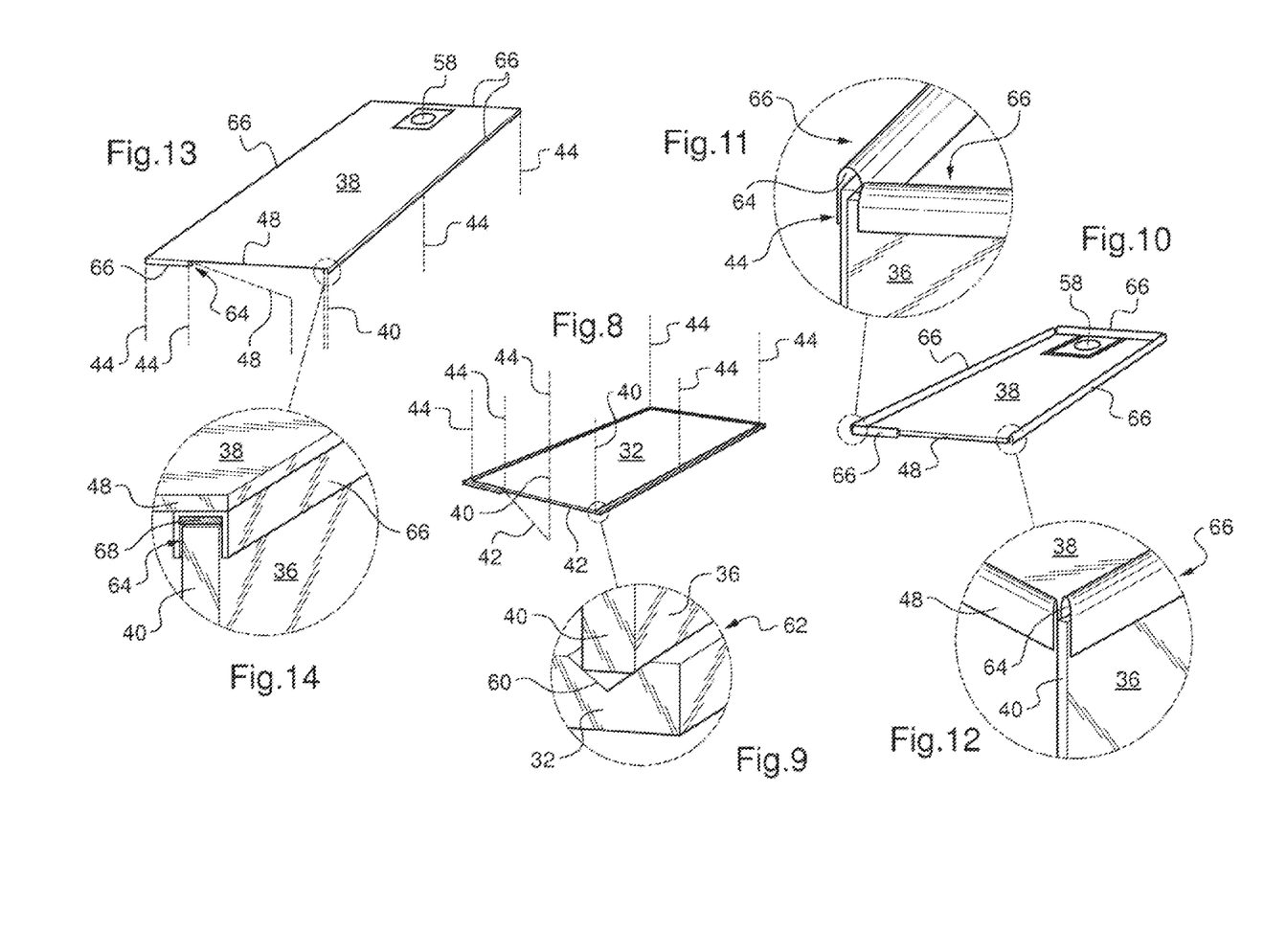
FIG. 8 shows a perspective view of an embodiment of the lower wall of the booth.
FIG. 9 shows an enlarged view of FIG. 8 at a join of the lower wall and one of the side walls of the booth.
FIG. 10 shows a perspective view of an embodiment of an upper wall of the booth.
FIGS. 11 and 12 show enlarged views of FIG. 10 at intersections between the joins of the walls of the booth.
FIG. 13 shows a perspective view of another embodiment of an upper wall of the booth.
FIG. 14 shows an enlarged view of FIG. 13 at the intersection of the joins of the walls.

According to another embodiment, the closing device between two adjacent walls 30 can comprise a groove. This embodiment of the closing device is preferred between adjacent walls the join of which is compressed in the position of use of the booth 20 under the effect of gravity. FIG. 8 shows the lower wall 32 on which the positioning of the side walls 34 and 36 is represented by broken lines at their joins 40, 42 and 44. According to the embodiment illustrated, the wall 32 is an airtight mat making it possible to level any unevennesses in the floor of the room in which the booth 20 is arranged. FIG. 9 shows an enlarged view of a detail from FIG. 8 at a join 62 of the lower wall 32 and one of the side walls 36. This join 62 comprises a V-shaped groove 60 as closing device between the side wall 36 and the lower wall 32. The V-shaped groove 60 facilitates the installation of the walls 30 of the booth which slide in the groove with lateral support within the groove. The airtightness of this join 62 is produced by the compression of the groove between the side wall 36 and the lower wall 32 under the effect of the weight of the wall 36. Similarly, an airtight closing device in the form of a groove 64 can be arranged at the joins 66 between the upper wall 38 and the side walls, as shown in FIGS. 10, 11 and 12, FIGS. 11 and 12 showing enlarged views of FIG. 10 at the intersections between the joins 44 and 66 and the joins 40, 48 and 66, respectively. The airtightness at the joins 66 is produced at the grooves 64 by the compression between the upper wall 38 and the side walls 36 under the effect of the weight of the upper wall 38.

FIG. 13 shows a perspective view of the upper wall 38 on which the positioning of the side walls 34 and 36 is represented by broken lines at their joins 40, 44 and 48, the closing device at the joins 66 comprising the groove 64. In a manner complementary to the embodiment comprising a groove or alternatively, the airtight closing devices can comprise a flat seal made of elastomer. FIG. 14 shows an enlarged view of FIG. 13 at the intersection of the joins 40, 48 and 66 with an elastomer 68 in the groove 64 of the join 66. The elastomer 68 is then compressed between the upper wall 38 and the wall 36 under the effect of the weight of the wall 38 thus ensuring a highly effective seal at the join 66.

As shown in FIGS. 4 and 5 in a general manner, the material used to produce the panels is preferably a cellular material in order to limit the total weight of the booth 20. Thus, according to a proposed embodiment, the weight of the booth 20 can be less than or equal to 25 kg, or even less than or equal to 23 kg. The reduction in weight of the booth 20 makes it easier for the booth 20 to be transported and handled by only one person while still respecting legal constraints. The material of the walls 30 can furthermore be chosen in order to limit the release of odour from an earlier sensory experiment. The material of the walls can thus be non-porous in order not to retain any residual traces of the aromas. Taking into account all of the functions previously mentioned for the booth 20, the material chosen for the walls is preferably cellular PVC such as Aquilux. The walls can have a thickness of 8 mm±2 mm, preferably ±1 mm.

The closed volume 22 of the proposed booth 20 can be suitable for all types of sensory analyses or tests. The booth 20 may thus comprise a removable shelf making it possible to provide equipment specific to the sensory analysis to be conducted: basin, spittoon, light box, computer system. FIG. 15 shows a shelf 70, previously shown in FIG. 2. The shelf 70 comprises articulated brackets 72 which can be placed flat as shown in FIG. 15 or as in FIG. 2 in the transport position. FIG. 16 shows the shelf with the brackets 72 in a perpendicular position ready to be installed in the booth in the position of use. FIG. 17 shows an enlarged view of a bracket 72 of the shelf 70 received in a support 74. The side walls 36 of the booth 20 can thus have such supports 74 in order to make it possible for the shelf 70 to be easily attached while ensuring a high degree of compactness of each wall 36 in the transport position of the booth 20.

In order to make it easier for equipment arranged inside the booth 20 to be connected to the outside a foam block comprising preformed holes is furthermore proposed. FIG. 18 shows such a foam block in the shape of a trapezoidal wedge 76 arranged in a corresponding opening in one of the side walls 36. FIG. 19 shows an enlarged view of the wedge 76. This wedge 76 is preferably made of high memory elastomer foam in order to allow it to be inserted in an airtight manner under compression in the corresponding opening in the wall 36. The airtight passage of wires or pipes 80 through the wedge 76, and thus out of the booth 20, takes place by means of star-shaped cut-outs 78 which can adapt to multiple elements of different sizes, shapes and sections, while maintaining the airtightness of the booth 20.

Different means have been described for sealing the closed volume of the booth 20 in the position of use. The booth 20 thus ensures a dearomatized atmosphere which is necessary for maintaining an olfactory experimental framework which is always identical and with a mobility allowed by the foldable nature of the booth.

However, the booth 20 both closed and in the position of use may also allow a circulation of air between the outside and the inside of the booth 20. This circulation of air between the inside and outside of the booth 20 is preferably controlled in order that the quality of the air inside the booth can be ensured thus allowing sensory analysis to be carried out. Thus, one or more walls 30 can be suitable for filtering the circulation of air through the wall 30. According to the embodiment shown in FIG. 6, the door 34 thus comprises a filter cartridge 90 comprising, for example, activated carbon mixed with fibres suitable for filtering the air circulating through the door 34. The door may comprise a movable grating 84 for accessing the cartridge in the door 34 in order to facilitate maintenance of the filter. The proposed filtration of the circulation of air between the inside and outside of the booth 20 is particularly useful for changing the air inside the booth 20 while limiting the introduction of interfering odours into the sensory analysis. In order to contribute to the controlled change of the air in the booth 20, the booth 20 may also be connected to a ventilation means, for example in order to extract air from the booth 20. According to the embodiment shown in FIG. 1, the booth 20 can thus be connected to a ventilation duct 82 making it possible to extract air from the booth 20. This ventilation duct 82 is, for example, connected to a controlled mechanical ventilation system 86, better known by the abbreviation CMV shown in FIG. 7. The connection of the CMV 86 to the booth 20 forms a system of sensory analysis which is also proposed. The air extracted by the CMV 86 may be evacuated through any opening of the premises in which the booth 20 is arranged, such as a window 88 or an air vent (not shown) of the premises. In the case where the premises in which the booth 20 is installed comprises such a window, a flexible blind for obscuring the window 88 can be provided in order to control the ambient lighting outside the booth 20. Controlling the lighting outside the booth 20 can be useful when the booth 20 has transparent walls, such as the pane 24 in the door 34, in order to avoid the user having too great a sense of being shut in the booth 20.

In order to facilitate the connection between the booth 20 and the ventilation duct 82 of the CMV 86, the booth 20 may comprise an opening suitable for being connected in an airtight manner to the ventilation duct 82. As shown in FIGS. 10 and 13, this opening 58 may be arranged in the upper wall 38. In order to ensure an airtight connection between the duct 82 and the booth 20, the opening 58 may be provided with a magnetic closing device as described previously for the joins 40, 42 and 48.

Of course, the present invention is not limited to the examples and the embodiment described and represented but is capable of numerous variants available to a person skilled in the art. In particular, the door 34 shown in FIG. 6 can comprise a stabilizing wheel 26 which limits warping of the door 34 while it is being moved between an open and closed position.

The invention claimed is:

1. Sensory isolation booth that is foldable between
 a folded transport position and
 an unfolded position of use forming a closed volume for receiving a user to perform a sensory analysis;
the booth comprising:
 walls, each wall being airtight or suitable for filtering the circulation of air through the wall;
 airtight articulations and closing devices positioned at the joint between walls, the articulations and closing devices, when closed, connecting the walls in an airtight manner in the unfolded position of use of the booth,
the folded articulations allowing the superposition of the walls on one another in the transport position of the booth, in which the walls comprise a first and a second wall made of the same common material, the first and the second walls being connected to each other in an airtight manner by the common material which is thinned locally in order to form one of the articulations.

2. Booth according to claim 1 in which the dimensions and the number of walls are chosen so that the closed reception volume in the position of use is greater than or equal to 1.9 $m^3$, and the volume of an external parallelepiped cover for the booth in the transport position is less than or equal to 0.5 $m^3$.

3. Booth according to claim 2, in which the dimensions and the number of walls are chosen so that the closed reception volume in the position of use is greater than or equal to 1.9 $m^3$ and the volume of an external parallelepiped cover for the booth in the transport position is less than or equal to 0.19 $m^3$.

4. Booth according to claim 2, in which the external parallelepiped cover for the booth in the transport position has a length less than or equal to 2.5 m, a width less than or equal to 1.5 m, and a depth less than or equal to 0.3 m.

5. Booth according to claim 4, in which the external parallelepiped cover for the booth in the transport position has a length less than or equal to 2 m, a width less than or equal to 1.1 m and a depth less than or equal to 0.1 m.

6. Booth according to claim 1, the weight of the booth being less than or equal to 25 kg.

7. Booth according to claim 1, in which the walls are made of a cellular material.

8. Booth according to claim 7, in which the walls are made of a cellular PVC.

9. Booth according to claim 1, in which the walls comprise wall forming a door or an access hatch to the closed reception volume, the door or the hatch comprising an airtight closing device.

10. Booth according to claim 1, in which the walls comprise:
 at least one horizontal wall comprising an upper wall;
 side walls;
the airtight closing devices of the booth comprising, at the join of the at least one horizontal wall and the side walls in the unfolded position of use of the booth, an airtight closing device comprising at least one elastomer seal and a groove the airtightness at the join of the at least one horizontal wall and the side walls being produced by compression of the airtight closing device between the side walls and the at least one horizontal wall under the effect of the weight of the walls.

11. Booth according to claim 1, in which the walls comprise a wall equipped with a filter cartridge suitable for filtering the air circulating through the said wall.

12. System for sensory analysis comprising:
 a controlled mechanical ventilation system;
 the booth according to claim 1, the booth comprising an opening suitable for being connected in an airtight manner to the controlled mechanical ventilation system in order to change the air in the closed reception volume in the position of use.

13. Booth according to claim 9, in which the airtight closing device closes magnetically.

14. Booth according to claim 10, in which the at least one horizontal wall comprises a lower wall.

\* \* \* \* \*